May 25, 1954 W. E. LAMMERTS Plant Pat. 1,279
ROSE PLANT
Filed March 2, 1953
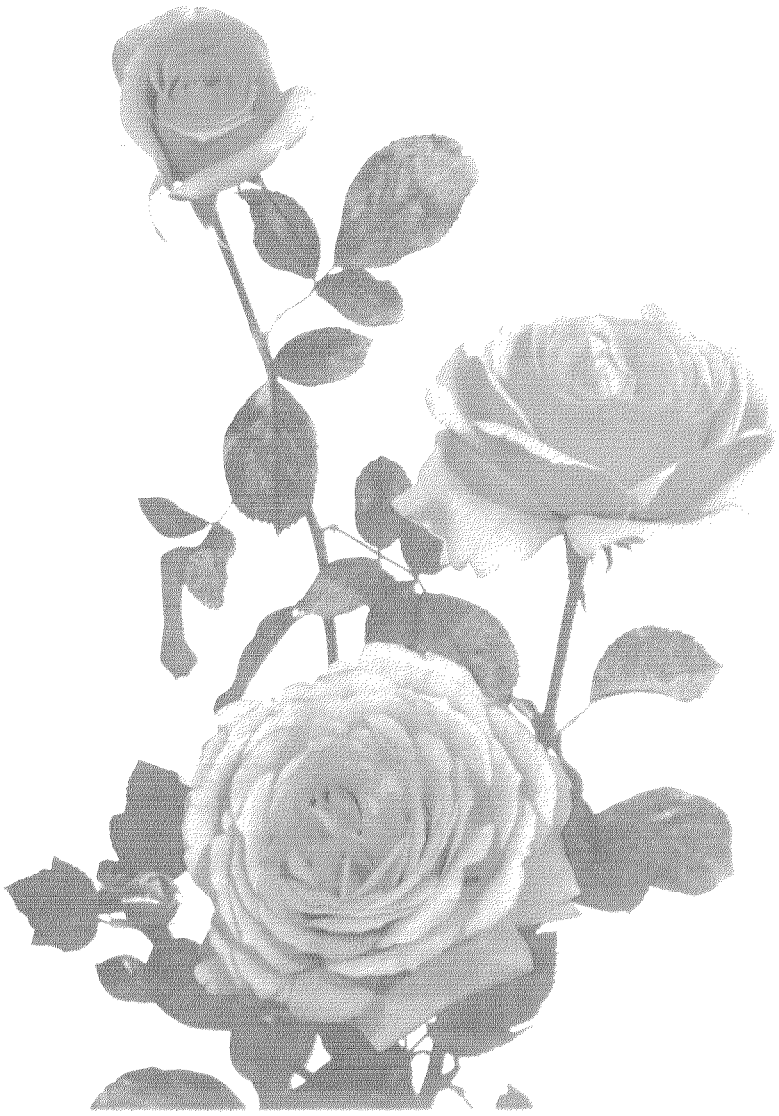
Inventor
W. E. Lammerts
By: Robert Cobb
Attorney.

Patented May 25, 1954 Plant Pat. 1,279

UNITED STATES PATENT OFFICE 1,279

ROSE PLANT

Walter E. Lammerts, La Canada, Calif., assignor to Roseway Nurseries, Portland, Oreg., a partnership consisting of Julia Hausch and Henry Hausch Application March 2, 1953, Serial No. 339,947

1 Claim. (Cl. 47—61)

The present invention relates to a new and distinct variety of rose plant of the hybrid tea class, which was originated by me by crossing the variety "Charlotte Armstrong" (Plant Patent No. 455) with the variety "Floradora" (unpatented).

As the result of the aforementioned cross, I have produced a new variety of rose plant which is distinctively different from its parents, as well as from all other varieties of its class, as evidenced by the following unique combination of outstanding characteristics:

(1) The very vigorous, much-branched and upright habits of growth;

(2) The abundance of glossy, dark green foliage;

(3) The heavy Pansy Purple tinge of the young growth and the Maroon Red tinge of the young shoots, which together give the plant a very attractive appearance even when not in flower;

(4) The floriferousness of the plant, as inherited from the pollen parent "Floradora";

(5) The relatively long cutting stems;

(6) The relatively large, very double flowers; and (7) The distinctive Claret Rose to Delft Rose general color tonality of the flowers which somewhat resembles the color of the flowers of the well-known variety "Tallyho" (Plant Patent No. 828), but from which my new variety is definitely distinguished by its glossy foliage, general habits of growth and other important differences, including its relative freedom from prickles and thorns, particularly in the upper portion of the plant and especially on the flowering shoots.

Asexual reproduction of my new variety by budding at La Canada, California, shows that the foregoing characteristics and distinctions come true to form and are established and transmitted through succeeding propagations.

The accompanying drawing shows typical specimens of the flowers, foliage and stems of my new variety in different stages of development.

The following is a detailed description of my new variety, with color terminology in accordance with the Horticultural Color Chart of the British Color Council, except where general color terms of ordinary dictionary significance are obvious:

Type: Hardy; dwarf; bush; outdoor; seedling; for garden decoration.

Class: Hybrid tea.

Breeding: Seedling.

*Seed parent.*—"Charlotte Armstrong."

*Pollen parent.*—"Floradora."

Propagation: Holds its distinguishing characteristics through succeeding propagations by budding.

*Flower*

Locality where grown and observed: La Canada, California.

Flowers borne: Singly and sometimes 2 or 3 to stem; on normal strength, medium length stems.

Quantity of bloom: Abundant, outdoors.

Continuity: Continuous.

Fragrance: Slight; centifolia.

Bud:

*Peduncle.*—Medium length; medium caliper; erect; smooth; no thorns, hairs or prickles, but almost entirely glabrous with occasional minute gland-tipped hairs. Color—dark bronze.

*Before calyx breaks.*—Size—small. Form—short; ovoid; without conspicuous neck; without foliaceous appendages on the surface of the bud; with serrate-margined foliaceous parts extending beyond the tip of the bud equal to about $\frac{1}{16}$ of its length. Color—almost black, shading to Oxblood Red, Plate 00823.

*As calyx breaks.*—Color—Indian Lake, Plate 826 at base, shading to Cherry, Plate 722, with upper portion Rose Opal, Plate 022, becoming Spirea Red, Plate 025 and tinged with China Rose, Plate 024 as bud continues opening.

*As first petal opens.*—Size—medium-large. Form — short; ovoid. Color — outside—Cardinal Red, Plate 822 at base, shading to Dark Rose Opal, Plate 022 to Spirea Red, Plate 025 in upper portions of petal; inside—Claret Rose, Plate 021 at base, shading to Rose Opal, Plate 022 and Spinel Red, Plate 0023 at margin of petal.

*Opening.*—Opens up well; is retarded from opening by cold weather.

Bloom:

*Size, when fully open.*—4½ inches to 5 inches.

*Petalage.*—Very double; from 50 to 55 petals; arranged somewhat irregularly.

*Form.*—Full, high center at first; as flower opens, petals are arranged in fairly regular imbricate manner, but when fully open, many inner petals and petaloids are irregularly arranged and often give a whorled appearance and very full, rather tightly packed petal arrangement; outer petals being at first tightly rolled inward, and becoming slightly rolled outward later at maturity.

Petals: Medium thin; with inside satiny and outside shiny.

*Shape.*—Outside—round-obovate; apex only about $\frac{1}{16}$ inch long and with 1 notch. Intermediate—obovate-elongate; with one slight notch about $\frac{1}{32}$ inch deep; intermediate petals usually strongly keeled.

This description of a newly opened flower was made from a rose grown outdoors in the month of October, at La Canada, California:

*Color.*—Outside petal: outside surface—Base China Rose, Plate 024, shading to Spirea Red, Plate 025/1; inside surface—Rose Opal, Plate 022, shading to Spinel Red, Plate 023 at margins of petal. Intermediate petal: outside surface—Crimson, Plate 22/1, shading to Spirea Red, Plate 025/1; inside surface—Delft Rose, Plate 020/1, shading to Rose Opal, Plate 022/1. Inner petal: outside surface—Crimson, Plate 22/1; inside surface—Claret Rose, Plate 021.

This description was made from a rose that was open for 3 days outdoors in the month of October, at La Canada, California:

*Color.*—Outside petal: outside surface—Spirea Red, Plate 025/1; inside surface—China Rose, Plate 024/2 to Spirea Red, Plate 025/2. Inside petal: outside surface—Tyrian Rose, Plate 24/1; inside surface—Spinel Pink, Plate 0625.

*General color effect.*—Newly opened flower—Claret Rose, Plate 021 to Delft Rose, Plate 020. Three days open—Spinel Pink, Plate 0625.

*Behavior.*—Drop off cleanly; color becomes more dull and ranges toward the light Spirea Red tones in cold weather.

*Flower longevity.*—On bush in garden—3 days in October. Cut roses grown outdoors and kept at living-room temperature—4 days in October.

*Reproductive organs*

Stamens: Medium number; arranged regularly about pistils; mixed with petaloids.

Filaments: Short; most with anthers. Color—Spirea Red, Plate 025/2.

Anthers: Small; open at various times. Color—Amber Yellow, Plate 505/1.

Pollen: Sparse. Color—gold.

Pistils: Medium number.

Styles: Very uneven; short; medium caliper; bunched.

Stigma: Color—Yellow, tinged with Spirea Red, Plate 025/3.

Ovaries: All enclosed in calyx.

Hips: Almost spherical; with inconspicuous neck; smooth: walls thin. Color—Majolica Yellow, Plate 09, and russeted toward base.

Sepals: Permanent; moderate length; straight at right angles to vertical axis of hip. Color—gray-brown.

*Plant*

Foliage:

*Leaves.*—Compound of 5 to 7 leaflets; very abundant; medium-large; moderately leathery; glossy.

*Leaflets.*—Shape—oval, with acute apex and round base; many terminal leaflets are slightly obovate. Margin—simply serrate.

*Color.*—Mature: upper surface—Parsley Green, Plate 00962 tinged with Pansy Purple, Plate 928/1; under surface—Willow Green, Plate 000862/1, strongly suffused with Pansy Purple, Plate 928/1. Young: upper surface—Parsley Green, Plate 00962/1, almost masked with Maroon, Plate 1030/1; under surface—Spinach Green, Plate 0960/3, heavily suffused with Pansy Purple, Plate 928/2.

*Rachis (the supporting stem of the compound leaf).*—Medium caliper. Upper side—smooth; shallowly grooved; hairy. Under side—extremely smooth; margins with gland-tipped hairs.

*Stipules.*—Moderately long; medium-narrow; with medium long points turning out at an angle of slightly less than 45°.

*Disease.*—Resistant to mildew, as determined by comparison with other varieties grown nearby under comparable cultural conditions and which were severely infected with mildew.

Growth:

*Habit.*—Dwarf; upright; much-branched.

*Growth.*—Free; vigorous.

*Canes.*—Heavy. Color—Parsley Green, Plate 00962/2.

*Main stems.*—Color—bright green. Thorns—comparatively few, and confined towards base of plant; medium length; straight; with long, narrow base. Prickles—none. Hairs—none.

*Branches.*—Color—Bright Willow Green, Plate 000862. Thorns—comparatively few; medium length; hooked downward; with long, narrow base. Prickles—none. Hairs—none.

*New shoots.*—Color—Oxblood Red, Plate 00823. Thorns—comparatively few; medium length; hooked downward; with long, narrow base. Prickles—none. Hairs—none.

I claim:

A new and distinct variety of rose plant of the hybrid tea class, substantially as herein shown and described, characterized particularly as to novelty by its vigorous, much-branched and upright habits of growth, by its abundance of glossy dark-green foliage, by the heavy tinge of Pansy Purple color in the young growth and by the Maroon Red tinge in the very young shoots, by its floriferousness and the relatively large size of its flowers which are borne on relatively long cutting stems, by the distinctive Claret Rose to Delft Rose general color tonality of its flowers, and by its relative freedom from prickles and thorns.

No references cited.